(12) United States Patent
Ichihashi et al.

(10) Patent No.: US 9,146,187 B2
(45) Date of Patent: Sep. 29, 2015

(54) VISCOELASTICITY MEASURING METHOD AND VISCOELASTICITY MEASURING APPARATUS

(75) Inventors: Motoko Ichihashi, Kanagawa (JP); Atsushi Itoh, Kanagawa (JP); Yukiko Yamamoto, Kanagawa (JP)

(73) Assignee: ULVAC, INC., Chigasaki (JP)

( * ) Notice: Subject to any disclaimer, the term of this patent is extended or adjusted under 35 U.S.C. 154(b) by 573 days.

(21) Appl. No.: 13/634,584

(22) PCT Filed: Mar. 14, 2011

(86) PCT No.: PCT/JP2011/001456
§ 371 (c)(1),
(2), (4) Date: Nov. 5, 2012

(87) PCT Pub. No.: WO2011/114684
PCT Pub. Date: Sep. 22, 2011

(65) Prior Publication Data
US 2013/0046487 A1    Feb. 21, 2013

(30) Foreign Application Priority Data
Mar. 16, 2010 (JP) .................................. 2010-059283

(51) Int. Cl.
*G01H 13/00* (2006.01)
*G01N 11/16* (2006.01)

(52) U.S. Cl.
CPC ........ *G01N 11/16* (2013.01); *G01N 2203/0008* (2013.01); *G01N 2203/0094* (2013.01)

(58) Field of Classification Search
None
See application file for complete search history.

(56) References Cited

U.S. PATENT DOCUMENTS 7,874,211 B2 *   1/2011   Itoh et al. ........................ 73/579
2004/0150428 A1   8/2004   Itoh
(Continued)

FOREIGN PATENT DOCUMENTS

JP      2004-325257 A1    11/2004
WO     WO 2007/004376 A1   1/2007

OTHER PUBLICATIONS

Markus Pax, Measurements of fast fluctuations of viscoelastic properties with the quartz crystal microbalance, 2005, 130, 1474-1477.*
Atsushi Itoh, A frequency of the quartz crystal microbalance (QCM) that is not affected by the viscosity of a liquid, 2008 IOP Publishing Ltd, 10 pages.*

(Continued)

*Primary Examiner* — Tung S Lau
(74) *Attorney, Agent, or Firm* — Kratz, Quintos & Hanson, LLP

(57) ABSTRACT

[Problem] A viscoelasticity measuring method and a viscoelasticity measuring apparatus are provided which can measure viscoelasticity of a sample substance even when the quantity of the sample substance is minute.
[Solution] A solution or semisolid sample substance is brought into contact with an electrode of a sensor formed of a quartz crystal oscillator, a variation $\Delta F_s$ of a resonance frequency $F_s$ of the quartz crystal oscillator and a variation $\Delta F_w$ of a half-value half frequency $(F_1-F_2)/2$ of a first frequency $F_1$ and a second frequency $F_2$ having conductance $\frac{1}{2} G_{max}$ which is a half of conductance $G_{max}$ of the resonance frequency $F_s$ are measured, and any of a storage elastic modulus G' of the sample substance based on the difference of squares of the variation $\Delta F_s$ of the resonance frequency and the variation $\Delta F_w$ of the half-value half frequency and a loss elastic modulus G" of the sample substance based on the multiplication of the variation $\Delta F_s$ of the resonance frequency and the variation $\Delta F_w$ of the half-value half frequency is calculated.

6 Claims, 4 Drawing Sheets

(56) References Cited

U.S. PATENT DOCUMENTS

2005/0164236 A1\* 7/2005 Su et al. ............................ 435/6
2005/0277111 A1\* 12/2005 Itoh et al. ......................... 435/4
2009/0038859 A1   2/2009 Itoh
2009/0165559 A1\* 7/2009 Lec ................................ 73/579

OTHER PUBLICATIONS

International Search Report for International Application No. PCT/JP2011/001456 dated Apr. 26, 2011.

\* cited by examiner

VISCOELASTICITY MEASURING METHOD AND VISCOELASTICITY MEASURING APPARATUS

TECHNICAL FIELD

The present invention relates to a method of measuring viscoelasticity of a solution or semisolid sample substance and a viscoelasticity measuring apparatus, which are used in the fields of chemistry, material, biochemistry, and physics.

BACKGROUND ART

A measuring apparatus using a QCM (Quartz Crystal Microbalance) in the related art is disclosed, for example, in PTL 1.

On the other hand, viscoelasticity measuring methods in the related art can be broadly classified into methods of a static viscoelasticity measuring method such as a steady flow measuring method or a uniform up and down method and a dynamic viscoelasticity measuring method in which a frequency function is deformed. Particularly, the dynamic viscoelasticity measuring method has been widely used, because information on viscosity or viscoelasticity can be acquired in a minutely-deformed state in which the measurement sample is not structurally destroyed.

However, when viscoelasticity is measured using a general viscoelasticity measuring apparatus, a measurement sample of at least 0.5 mL to 50 mL is necessary. A measuring method suitable for measuring viscoelasticity of substances, which cannot be taken in large quantity, such as substances taken in minute quantity from a human body or grease used in a machine actually working does not exist.

CITATION LIST

Patent Literature

[PTL 1] JP-A-2009-36644

SUMMARY OF INVENTION

Technical Problem

Therefore, an object of the invention is to provide a measuring method and a measuring apparatus which can measure viscoelasticity of a sample substance even when the quantity of the sample substance is minute.

Solution to Problem

According to the invention of Claim 1, there is provided a viscoelasticity measuring method, including the steps of: bringing a solution or semisolid sample substance into contact with an electrode of a sensor formed of a quartz crystal oscillator; measuring a variation $\Delta F_s$ of a resonance frequency $F_s$ of the quartz crystal oscillator and a variation $\Delta F_w$ of a half-value half frequency $(F_1-F_2)/2$ of a first frequency $F_1$ and a second frequency $F_2$ having conductance $\frac{1}{2} G_{max}$ which is a half of conductance $G_{max}$ of the resonance frequency $F_s$; and calculating any of a storage elastic modulus G' of the sample substance based on the difference of two squares of the variation $\Delta F_s$ of the resonance frequency and the variation $\Delta F_w$ of the half-value half frequency and a loss elastic modulus G" of the sample substance based on the multiplication of the variation $\Delta F_s$ of the resonance frequency and the variation $\Delta F_w$ of the half-value half frequency.

The invention of Claim 2 provides the viscoelasticity measuring method, wherein the storage elastic modulus G' is expressed by Expression 1, and the loss elastic modulus G" is expressed by Expression 2:

$$G' = \frac{(\Delta Fw^2 - \Delta Fs^2)}{\rho_v} \cdot \left(\frac{F_0}{\pi Z_q}\right)^2 \quad \text{Expression 1}$$

$$G'' = \frac{2 \cdot \Delta Fs \cdot \Delta Fw}{\rho_v} \cdot \left(\frac{F_0}{\pi Z_q}\right)^2 \quad \text{Expression 2}$$

wherein $Z_q$ represents a shearing stress of the quartz crystal oscillator, $\rho_v$ represents a density of the sample substance, and $F_0$ represents a fundamental vibration frequency.

The invention of Claim 3 provides the viscoelasticity measuring method, wherein the measurement frequency is set to a fundamental wave or an overtone (a threefold wave, a fivefold wave, a sevenfold wave, . . . ) of the quartz crystal oscillator.

The invention of Claim 4 provides the viscoelasticity measuring method, wherein the sample substance is brought into contact with only the electrode.

The invention of Claim 5 provides the viscoelasticity measuring method, wherein the volume of the sample substance is set to 100 μL or less.

According to the invention of Claim 6, there is provided a viscoelasticity measuring apparatus, including: a sensor formed of a quartz crystal oscillator; measurement means for measuring a variation $\Delta F_s$ of a resonance frequency $F_s$ of the quartz crystal oscillator and a variation $\Delta F_w$ of a half-value half frequency $(F_1-F_2)/2$ of a first frequency $F_1$ and a second frequency $F_2$ having conductance $\frac{1}{2} G_{max}$ which is a half of conductance $G_{max}$ of the resonance frequency $F_s$; and calculation means for calculating the difference of squares of the variation $\Delta F_s$ of the resonance frequency and the variation $\Delta F_w$ of the half-value half frequency and the multiplication of the variation $\Delta F_s$ of the resonance frequency and the variation $\Delta F_w$ of the half-value half frequency.

Advantageous Effects of Invention

According to the invention, it is possible to measure the viscoelastic modulus of a solution or semisolid sample substance, for example, even when the quantity of the sample substance is equal to or less than 100 μL. An overtone can be effectively used to reduce a standing wave (see JP-A-2005-098866) generated when agitation cannot be performed for measurement of a minute quantity and it is thus possible to perform measurement with high precision. It is also possible to perform measurement on a smaller amount of a sample by bringing the sample substance into contact with only an electrode of a sensor.

DESCRIPTION OF EMBODIMENTS

Viscoelasticity in the invention means a property or a state including both a solid elastic component and liquid viscous component.

Viscoelasticity is expressed by a complex viscoelastic modulus G* which is a complex number of G' (storage elastic modulus) and G" (loss elastic modulus) as shown in Expression 3.

$$G^* = G' + jG''$$ Expression 3

The storage elastic modulus (G') is a component in which deformation energy is accumulated as a stress in a substance, which represents an elastic component of the substance. The loss elastic modulus (G") is a component in which energy given to the substance is converted into other energy such as heat and is lost, which represents a viscous component of the substance.

A substance having this viscoelasticity is a substance to be measured in the invention and examples thereof include a polymer solution, a colloid solution, a gel, and a rubber.

Figure 1:
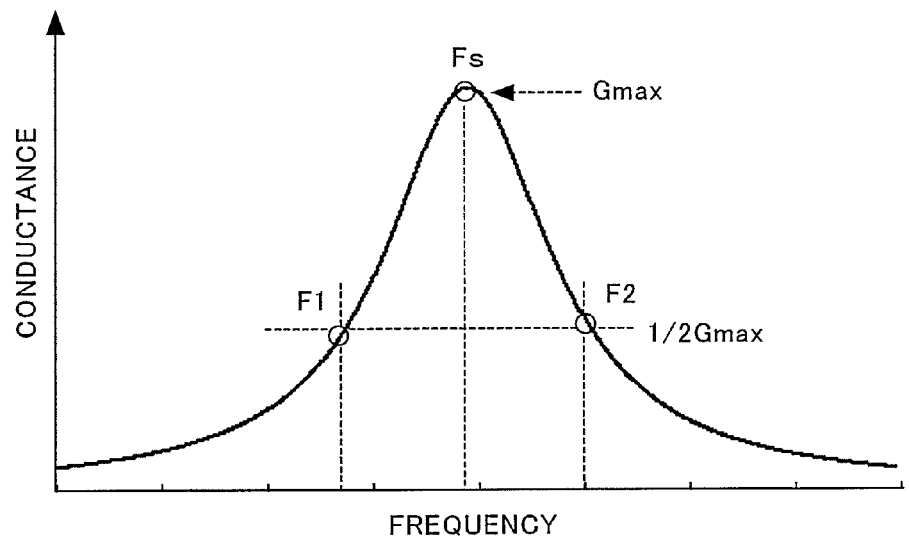
FIG. 1 is a diagram illustrating a resonance frequency $F_s$ and first and second frequencies $F_1$ and $F_2$.

In the invention, the viscoelastic modulus of a sample substance is measured on the basis of variation $\Delta F_s$ of the resonance frequency $F_s$ and the variation $\Delta F_w$ of the half-value half frequency $(F_1-F_2)/2$ in the conductance waveform of the resonance frequency $F_s$ when the sample substance is brought into contact with a quartz crystal oscillator and is made to vibrate with a fundamental wave by the use of a measuring apparatus using a QCM. As shown in FIG. 1, $F_1$ and $F_2$ mean a first frequency $F_1$ and a second frequency $F_2$ ($F_1 < F_2$) providing the resonance frequency $F_s$ at which the quartz crystal oscillator is in a series state and the half conductance which is a half $G_{max}/2$ of the conductance $G_{max}$ when the quartz crystal oscillator is in the resonant state.

The viscoelastic moduli G' and G" of a solution or a semisolid are expressed by Expression 4 and Expression 5 using the above-mentioned values.

$$\Delta Fs = -\frac{F_0}{\pi Z_q}\sqrt{\frac{\rho_v(|G^*|-G')}{2}}$$ Expression 4

$$\Delta\frac{(F1-F2)}{2} = \Delta Fw = -\frac{F_0}{\pi Z_q}\sqrt{\frac{\rho_v(|G^*|+G')}{2}}$$ Expression 5

In the expressions, $Z_q$ represents a shearing stress (gm/sec/cm$^2$) of the quartz crystal oscillator, $\rho_v$ represents a density (g/cm$^3$) of the sample substance, and $F_0$ represents a fundamental vibration frequency.

By measuring the frequency variations of $\Delta F_s$ and $\Delta(F_1-F_2)/2$ and substituting the density of a solution or a semisolid, the viscoelastic moduli G' and G" can be calculated as follows.

$$G' = \frac{(\Delta Fw^2 - \Delta Fs^2)}{\rho_v} \cdot \left(\frac{F_0}{\pi Z_q}\right)^2$$ Expression 6

$$G'' = \frac{2 \cdot \Delta Fs \cdot \Delta Fw}{\rho_v} \cdot \left(\frac{F_0}{\pi Z_q}\right)^2$$ Expression 7

As described above, G' (storage elastic modulus) and G" (loss elastic modulus) can be calculated from the difference of squares $(\Delta F_w^2 - \Delta F_s^2)$ and the multiplication $(\Delta F_s \cdot \Delta F_s)$.

In the measurement, the resonance frequency based on the fundamental wave may be measured, but an overtone (a N-fold wave, where N=3, 5, 7, . . . ) can be preferably used when performing measurement on a small amount of sample which cannot be agitated. This is because the standing wave generated at the time of measurement can be reduced and it is thus possible to perform measurement with high precision. The resonance frequency includes frequencies around the resonance frequency and includes, for example, scanning the range of ±500 kHz thereof.

Figure 2:
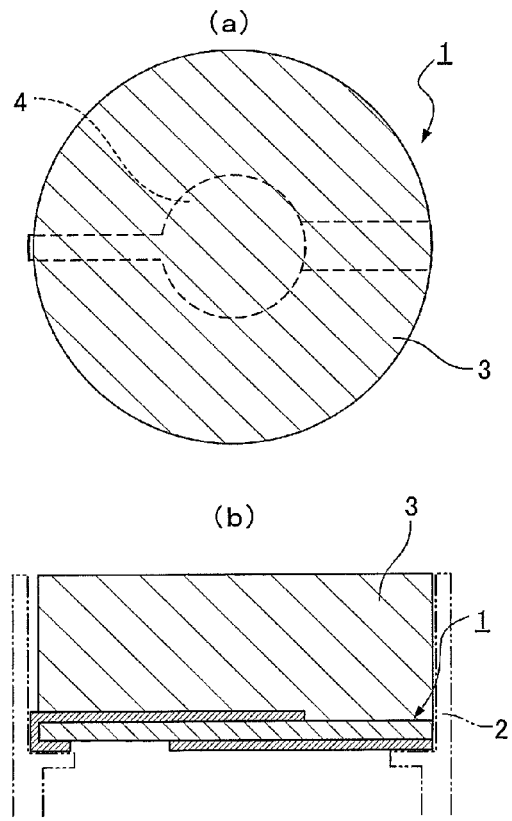
FIG. 2 is a diagram illustrating an example of a sample substance in a measuring method according to the invention (where FIG. 2(a) is a plan view and FIG. 2(b) is a cross-sectional view).

In the measuring method according to the invention, the quantity of a sample substance is not particularly limited. A sample substance 3 may be injected into a structure in which a quartz crystal oscillator 1 is disposed on the bottom of a vessel 2 as shown in FIG. 2 or a sample substance 5 may be brought into contact with only an electrode 4 of the quartz crystal oscillator 1 as shown in FIG. 3.

Figure 3:
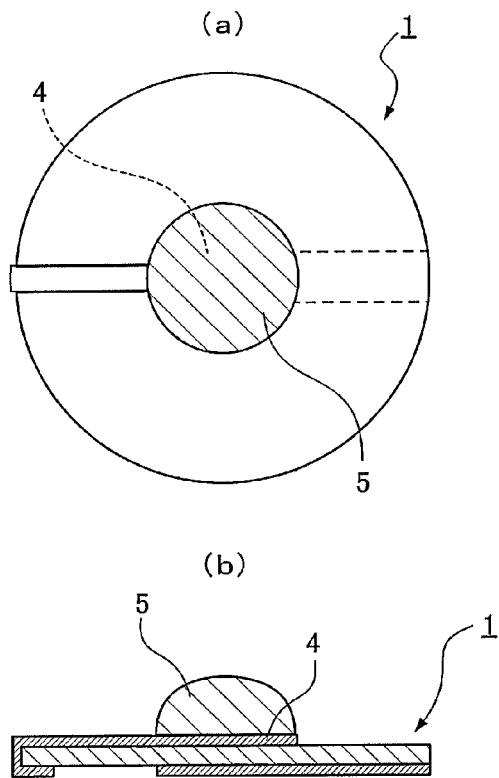
FIG. 3 is a diagram illustrating another example of a sample substance in a measuring method according to the invention (where FIG. 3(a) is a plan view and FIG. 3(b) is a cross-sectional view).

In the quartz crystal oscillator 1, since the sensitivity is concentrated on only the part of the central electrode 4, the sample substance is preferably brought into contact with only the electrode 4 as shown in FIG. 3. In this case, the quantity of the sample substance 3 depends on the diameter of the electrode 4. When the diameter is 2.5 mm, it is possible to perform measurement with an ultralow volume of liquid of 10 μL.

Since the penetration depth of thickness-shear vibration in pure water is about 0.1 μm in a 27 MHz quartz crystal oscillator and is about 0.2 μm in a 5 MHz quartz crystal oscillator, it can be seen that 100 μL of the sample substance is sufficient to cover the electrode of the quartz crystal oscillator and approximately several mm of a semisolid substance such as gel or grease is sufficient to cover the electrode.

The measuring method according to the invention will be described below in more detail.

Figure 4:
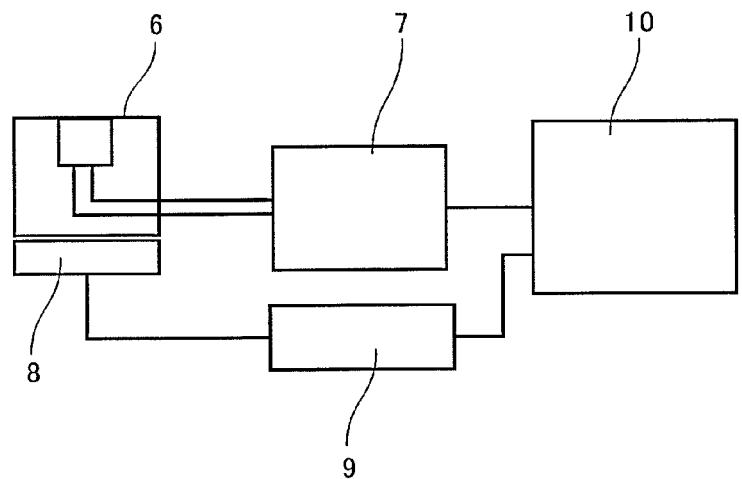
FIG. 4 is a diagram illustrating a measuring apparatus according to an embodiment of the invention.

The measuring apparatus shown in FIG. 4 includes measurement means constituted by a sensor unit 6 including a quartz crystal oscillator and a network analyzer 7 and temperature control means constituted by a Peltier device 8 disposed below the sensor unit 6 so as to control the temperature of the sensor unit 6 and a Peltier controller 9 and is connected to a computer 10 including control means for controlling the units, display means for displaying the measurement result and the like, calculation means including a central processing unit calculating Expressions 6 and 7 on the basis of the measurement result, and storage means including a RAM and a ROM.

Figure 5:
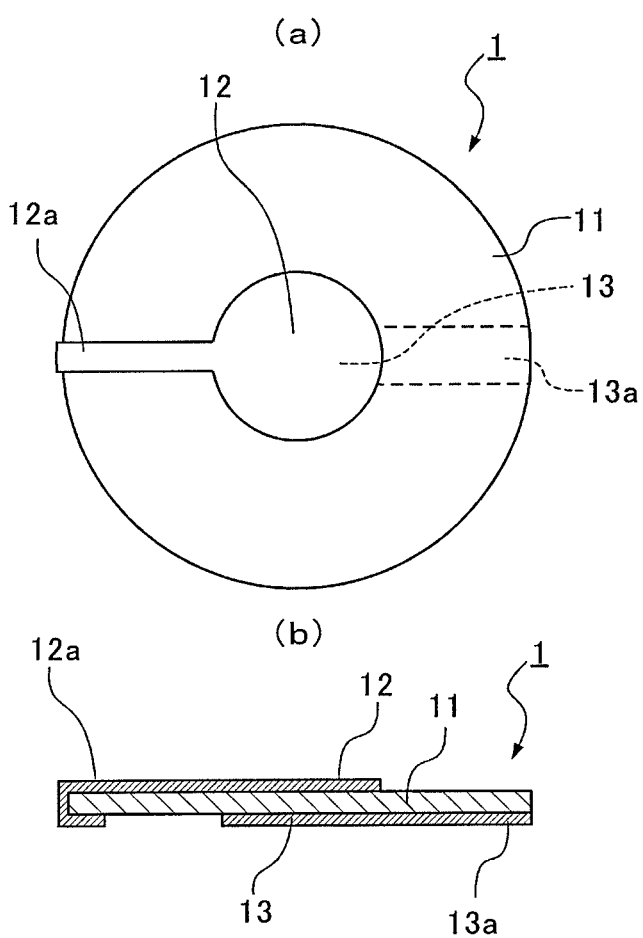
FIG. 5 is a diagram illustrating a quartz crystal oscillator used in the measuring apparatus according to the invention (where FIG. 5(a) is a plan view and FIG. 5(b) is a cross-sectional view).

As shown in the plan view and the cross-sectional view of FIGS. 5(a) and 5(b), the quartz crystal oscillator 1 of the sensor unit 2 includes a quartz crystal plate 11 having a circular shape and a first gold electrode 12 and a second gold electrode 13 disposed on the front surface and the rear surface of the plate 11. The gold electrodes 12 and 13 have a circular shape and lead lines 12a and 13a are connected thereto. The second gold electrode 13 on the rear surface is coated with a resin cover not shown, so that the second gold electrode 13 on the rear surface can vibrate without being exposed to the solution even in the state where the quartz crystal oscillator 1 is immersed in the solution.

The network analyzer 7 includes a signal supply circuit and a measurement circuit. The signal supply circuit is configured to output an AC input signal while changing the frequency. The measurement circuit is configured to measure electric characteristics such as the resonance frequency and the phase of the quartz crystal oscillator 1 on the basis of the output signal of the quartz crystal oscillator 1 and the input signal output from the signal supply circuit and to output the measured electric characteristics to the computer 10.

By employing the above-mentioned configuration, it is possible to measure $\Delta F_s$ and $\Delta F_w$ when a measuring target comes in contact with the quartz crystal oscillator and to calculate at least one of G' and G" using Expressions 6 and 7.

EXAMPLES

Hereinafter, an example of the invention will be described.

In the apparatus configuration shown in FIG. 4, a measurement example where a 27 MHz quartz crystal oscillator 1 with a gold electrode 12 of a diameter of 2.5 mm is used will be described below.

10 µL of a bovine serum albumin (BSA) solution (with concentrations of 50 mg/mL, 75 mg/mL, 100 mg/mL, 150 mg/mL, and 200 mg/mL) was placed on the washed gold electrode 12 and the variations of $\Delta F_s$ and $\Delta F_w$ were measured. The measurement results are shown in Table 1.

TABLE 1

| Concentration of BSA (mg/mL) | $\Delta F_s$ (Hz) | $\Delta F_w$ (Hz) |
|---|---|---|
| 0 | −9040 | −9005 |
| 50 | −10525 | −10300 |
| 75 | −10990 | −11003 |
| 100 | −11740 | −11898 |
| 150 | −13493 | −14083 |
| 200 | −15035 | −16513 |

Figure 6:
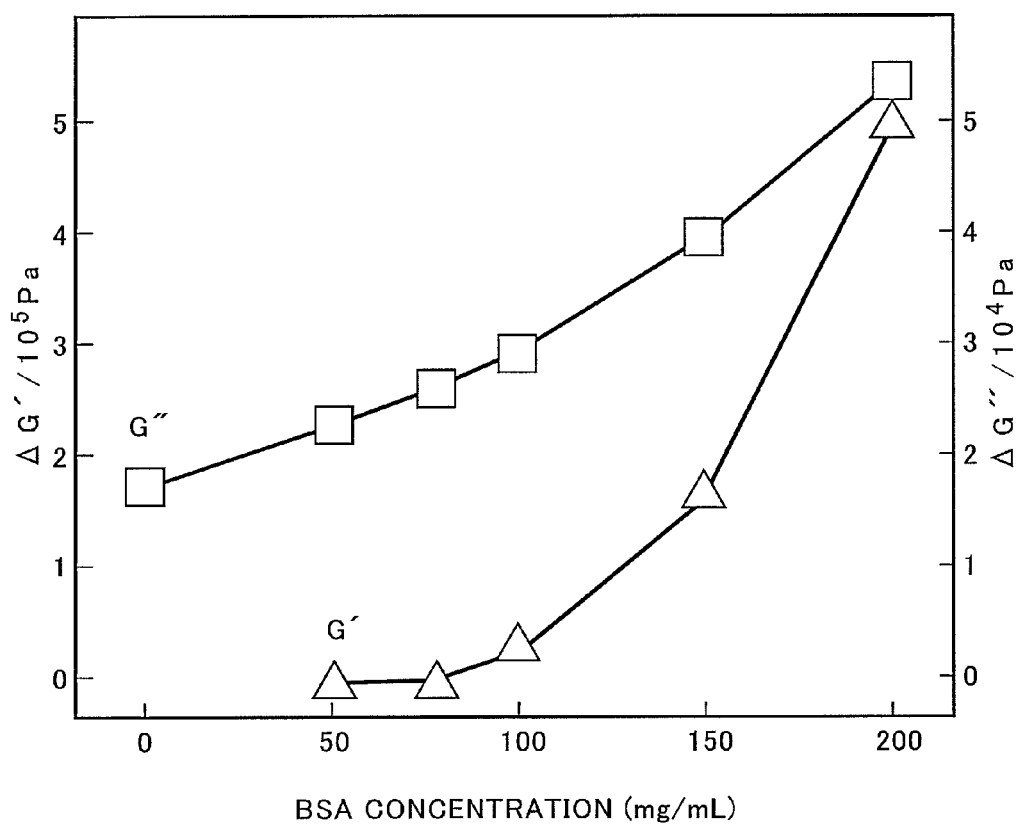
FIG. 6 is a graph illustrating the measurement result of the measuring method according to an embodiment of the invention.

The calculation results of G' and G" using the frequency variations and the density (assumed as 1 because almost all thereof is occupied by pure water) of the bovine serum albumin (BSA) solution are shown in FIG. 6.

By employing the measuring method according to the invention, it can be seen from FIG. 6 that G' and G" of the viscoelasticity can be accurately measured even from 10 µL of the sample substance (corresponding to one droplet of a dropper).

INDUSTRIAL APPLICABILITY

The invention can be widely used to measure viscoelasticity of a solution or a semisolid in the fields of chemistry, material, biochemistry, and physics.

REFERENCE SIGNS LIST

1: QUARTZ CRYSTAL OSCILLATOR
2: VESSEL
3, 5: SOLUTION
4, 12: (FIRST) ELECTRODE
6: SENSOR UNIT
7: NETWORK ANALYZER
8: PELTIER DEVICE
9: PELTIER CONTROLLER
10: COMPUTER
12a, 13a: LEAD PORTION
13: (SECOND) ELECTRODE

The invention claimed is:

1. A viscoelasticity measuring method, comprising the steps of:
   bringing a solution or semisolid sample substance into contact with an electrode of a sensor formed of a quartz crystal oscillator;
   measuring a variation $\Delta F_s$ of a resonance frequency $F_s$ of the quartz crystal oscillator and a variation $\Delta F_w$ of a half-value half frequency $(F_1-F_2)/2$ of a first frequency $F_1$ and a second frequency $F_2$ having conductance ½ $G_{max}$ which is a half of conductance $G_{max}$ of the resonance frequency $F_s$; and
   calculating any of a storage elastic modulus G' of the sample substance based on the difference of squares of the variation $\Delta F_s$ of the resonance frequency and the variation $\Delta F_w$ of the half-value half frequency and a loss elastic modulus G" of the sample substance based on the multiplication of the variation $\Delta F_s$ of the resonance frequency and the variation $\Delta F_w$ of the half-value half frequency.

2. The viscoelasticity measuring method according to claim 1, wherein the storage elastic modulus G' is expressed by Expression 1, and the loss elastic modulus G" is expressed by Expression 2:

$$G' = \frac{(\Delta Fw^2 - \Delta Fs^2)}{\rho_v} \cdot \left(\frac{F_0}{\pi Z_q}\right)^2 \qquad \text{Expression 1}$$

$$G'' = \frac{2 \cdot \Delta Fs \cdot \Delta Fw}{\rho_v} \cdot \left(\frac{F_0}{\pi Z_q}\right)^2 \qquad \text{Expression 2}$$

wherein $F_0$ represents a fundamental vibration frequency, $Z_q$ represents a shearing stress of the quartz crystal oscillator, and $\rho_v$ represents a density of the sample substance.

3. The viscoelasticity measuring method according to claim 1, wherein the measurement frequency is set to a fundamental wave or an overtone (a threefold wave, a fivefold wave, a sevenfold wave, . . . ) of the quartz crystal oscillator.

4. The viscoelasticity measuring method according to claim 1, wherein the sample substance is brought into contact with only the electrode.

5. The viscoelasticity measuring method according to claim 1, wherein the volume of the sample substance is set to 100 µL or less.

6. A viscoelasticity measuring apparatus, comprising:
   a sensor formed of a quartz crystal oscillator;
   measurement means for measuring a variation $\Delta F_s$ of a resonance frequency $F_s$ of the quartz crystal oscillator and a variation $\Delta F_w$ of a half-value half frequency $(F_1-F_2)/2$ of a first frequency $F_1$ and a second frequency $F_2$ having conductance ½ $G_{max}$ which is a half of conductance $G_{max}$ of the resonance frequency $F_s$; and
   calculation means for calculating the difference of squares of the variation $\Delta F_s$ of the resonance frequency and the variation $\Delta F_w$ of the half-value half frequency and the multiplication of the variation $\Delta F_s$ of the resonance frequency and the variation $\Delta F_w$ of the half-value half frequency.

* * * * *